(12) United States Patent
Polebitski et al.

(10) Patent No.: US 11,022,721 B2
(45) Date of Patent: Jun. 1, 2021

(54) SPATIALLY DIVERSE SNOWPACK SENSING SYSTEM

(71) Applicant: WiSys Technology Foundation, Inc., Madison, WI (US)

(72) Inventors: Austin S. Polebitski, Platteville, WI (US); James Pelegrin, Platteville, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 116 days.

(21) Appl. No.: 16/441,707

(22) Filed: Jun. 14, 2019

(65) Prior Publication Data

US 2019/0383967 A1 Dec. 19, 2019

Related U.S. Application Data

(60) Provisional application No. 62/685,525, filed on Jun. 15, 2018.

(51) Int. Cl.
| | |
|---|---|
| *G01W 1/14* | (2006.01) |
| *G01B 17/02* | (2006.01) |
| *G01K 11/22* | (2006.01) |
| *G01N 33/18* | (2006.01) |
| *G01G 23/37* | (2006.01) |

(52) U.S. Cl.
CPC .............. *G01W 1/14* (2013.01); *G01B 17/02* (2013.01); *G01G 23/3735* (2013.01); *G01K 11/22* (2013.01); *G01N 33/18* (2013.01); *G01N 2033/1873* (2013.01)

(58) Field of Classification Search
None
See application file for complete search history.

(56) References Cited

U.S. PATENT DOCUMENTS

| | | | | |
|---|---|---|---|---|
| 5,594,250 | A  * | 1/1997 | Condreva | G01T 1/178 250/361 R |
| 8,552,396 | B2 * | 10/2013 | Frolik | G01V 5/02 250/393 |
| 8,746,056 | B2 * | 6/2014 | Jung | G01N 15/0205 73/170.17 |
| 9,465,020 | B2 * | 10/2016 | Christian | G01N 3/00 |
| 9,587,974 | B2 * | 3/2017 | Wechselberger | G01G 23/3735 |
| 9,958,346 | B2 * | 5/2018 | Kubicek | G01P 13/02 |
| 10,634,609 | B2 * | 4/2020 | Johnson | G01W 1/10 |
| 2019/0107646 | A1 * | 4/2019 | Trustman | G01G 17/04 |

FOREIGN PATENT DOCUMENTS

DE    102006014813 B3 *  9/2007    .........  G01G 23/3728

* cited by examiner

*Primary Examiner* — Peter J Macchiarolo
*Assistant Examiner* — Jermaine L Jenkins
(74) *Attorney, Agent, or Firm* — Boyle Fredrickson S.C.

(57) ABSTRACT

Multiple spatially diverse and compact weight sensors are statistically combined to reduce or eliminate errors caused by snow bridging. Data transmission using satellite communication minimizes the power consumption of the sensor station further allowing the entire system to be relatively compact and easily transported. The weight sensors may be combined with other standard sensors for measurement of air temperature and snow height, the latter measurement, for example, using ultrasound ranging or the like.

18 Claims, 1 Drawing Sheet

SPATIALLY DIVERSE SNOWPACK SENSING SYSTEM

CROSS REFERENCE TO RELATED APPLICATION

This application claims the benefit of U.S. Provisional Application No. 62/685,525, filed Jun. 15, 2018 and hereby incorporated by reference.

STATEMENT REGARDING FEDERALLY SPONSORED RESEARCH OR DEVELOPMENT

- -

BACKGROUND OF THE INVENTION

The present invention relates generally to snowpack sensors, and in particular, to a snowpack sensor having improved portability and reduced cost.

The measurement of snowpack, being the accumulation of snow, for example, upstream of a watershed, plays an important role in water management. For this purpose, snowpack sensors have been developed which attempt to automatically determine snow-water equivalents (SWE) of a snowpack to provide estimates of water stored in that snowpack.

A typical snowpack sensor may provide for a "snow pillow" being a fluid-filled bladder (rubber or galvanized metal) connected to a pressure sensor so that the signal from the pressure sensor may be used to determine the weight of snow overlying the pillow. The snow pillow intentionally occupies a relatively large area (e.g., greater than 10 feet in diameter) in order to resist the effects of so-called "snow bridges" where the weight of snowpack is conducted away from the surface of the snow pillow into the surrounding terrain by a bridge or lens of snow producing an erroneously low snowpack reading.

The snow pillow may be employed together with temperature sensors and a snowpack height sensor, for example, using ultrasonic range finding radar or the like to measure the snow height. This measure of snow height together with snow weight can provide for useful density information.

Snowpack sensor systems are typically remote from cell phone towers and the like and, accordingly, data from the snowpack sensor may be transmitted by meteor burst technology in which radio signals are reflected off of ionization caused by meteors.

SUMMARY OF THE INVENTION

The present invention greatly reduces the cost and bulk of a snowpack sensing system by replacing the large snow pillow with multiple spatially diverse and compact weight sensors that are statistically combined to reduce or eliminate errors caused by snow bridging. Data transmission using satellite communication minimizes the power consumption of the sensor station further allowing the entire system to be relatively compact and easily transported. The weight sensors may be combined with other standard sensors for measurement of air temperature and snow height, the latter measurement, for example, using ultrasound ranging or the like.

Specifically, one embodiment of the present invention provides a snowpack measuring system including an array of at least two weight plates positioned in horizontal separation along a plane of ground in an array region, each weight plate including an upper plate for receiving snow thereon and positioned above a base plate and separated from the base plate by at least one load cell providing a weight signal indicating a weight on the upper plate; and a processor receiving the weight signal from the load cells of each of the at least two weight plates and executing a program stored in non-transitory memory to combine the weight signals from the at least two weight plates to provide a weight representation of the snowpack in the array region.

It is thus a feature of at least one embodiment of the present invention to provide a compact snowpack measurement system by employing an array of smaller sensors.

The array region may have an area that is less than 10 m×10 m. An area of each of the at least two weight plates may be between 1 square foot and 4 square feet.

It is thus a feature of at least one embodiment of the present invention to reduce the cost and bulk of a large single "snow pillow" snowpack measuring system.

The processor may execute the program stored in memory to average the weight signals of the at least two weight plates to provide an average weight measurement.

It is thus a feature of at least one embodiment of the present invention to provide the benefits of a broad area measurement system like the snow pillow while using multiple smaller sensors.

The system may include at least three weight plates and the processor may execute the program stored in memory to identify an outlier weight signal deviating by more than a predetermined percentage threshold from the weight representation of the at least three weight plates and removing the outlier weight signal from the weight representation.

It is thus a feature of at least one embodiment of the invention to overcome the problem of snow bridges that can provide erroneous readings on smaller sensors.

The processor may execute the program stored in memory to analyze a time series of weight change on the weight plates to reveal an occurrence of a snow bridge formation conducting a weight of the snow away from the weight plates.

It is thus a feature of at least one embodiment of the invention to provide a method of detecting snow bridges that may not be evident in a static analysis but can be revealed by analyzing changes over time.

The processor may execute the program stored in memory to analyze off-center loads on the weight plates to reveal an occurrence of a snow bridge formation.

It is thus a feature of at least one embodiment of the present invention to identify snow bridge formations and eliminate sensors associated with such formations based on uneven loading that can occur with the snow bridge.

A control unit may communicate with the at least two weight plates and may include an antenna configured for over-the-air transmission of data.

It is thus a feature of at least one embodiment of the present invention to minimize the power consumption of the sensor station.

A solar panel may provide power to the control unit.

It is thus a feature of at least one embodiment of the present invention to be relatively compact and easily transported.

A height sensor may measure a height of the snow above the base plate and may be configured to communicate the height to the control unit.

It is thus a feature of at least one embodiment of the present invention to provide useful snow density information.

A GPS system may communicate a location signal through the antenna representing a location of the weight plate.

It is thus a feature of at least one embodiment of the present invention to help locate the snowpack measurement site which may be obscured or buried by snow.

The load cells may be arranged at corners of the weight plate and may be configured to support the upper plate over the base plate. The load cells may be covered by a flexible membrane providing protection from the elements. The weight plates may be held to the ground by the downwardly extending spikes.

It is thus a feature of at least one embodiment of the present invention to provide detection of off-center loads and prevent displacement of the weight plates.

A temperature sensor measuring an air temperature may be configured to communicate the air temperature to the control unit.

It is thus a feature of at least one embodiment of the present invention to provide useful information at the snow measurement site.

In an alternative embodiment of the present invention, a method of measuring an accumulation of snow in a region includes placing an array of at least two weight plates in separation along a substantially horizontal plane of the ground and each weight plate including an upper plate for receiving snow thereon and separated from a base plate by load cells measuring a weight on the upper plate; receiving a weight signal from the load cells of each of the at least two weight plates representing the weight on the upper plate; and combining the weight signals from the at least two weight plates to provide a weight representation of the snowpack in a region of the array.

These particular objects and advantages may apply to only some embodiments falling within the claims and thus do not define the scope of the invention.

DETAILED DESCRIPTION OF THE PREFERRED EMBODIMENT

Figure 1:
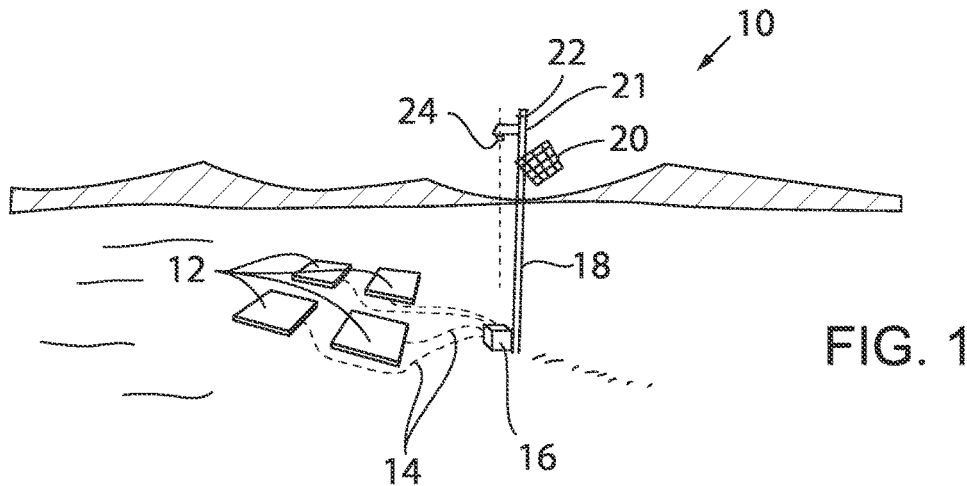
FIG. 1 is a perspective view of an installation of the present invention providing multiple, spatially separated weight plates.

Referring now to FIG. 1, a snowpack measurement site 10 employing the present invention may provide for an array of weight plates 12 separated from each other to reduce the chance of a single snow bridge spanning more than one weight plate 12 but also clustered within approximately 10 meters by 10 meters over which snowpack is believed to be approximately homogenous. In this way the data from each weight plate 12 may be used cumulatively to provide a better assessment of snowpack weight. Each of the weight plates 12e, for example, may have an area from 1 to 4 square feet and much less than the 50 square feet minimum required of the snow pillow.

The weight plates 12 may communicate by underground service cabling 14 to a control unit 16. The control unit 16 may be placed near a tower pole 18, for example, the latter embedded in the ground and extending upward to a height above the maximum expected snowpack height. The tower pole 18 may support a solar panel 20 providing power to the control unit 16, an air temperature sensor 21, and an antenna 22 for the transmission of data eliminating the need for a separate antenna structure. The tower pole 18 may also support a downwardly directed snowpack height sensor 24 such as an ultrasound range sensor providing a measure of the height of the snowpack above the base of the tower pole 18.

Figure 2:
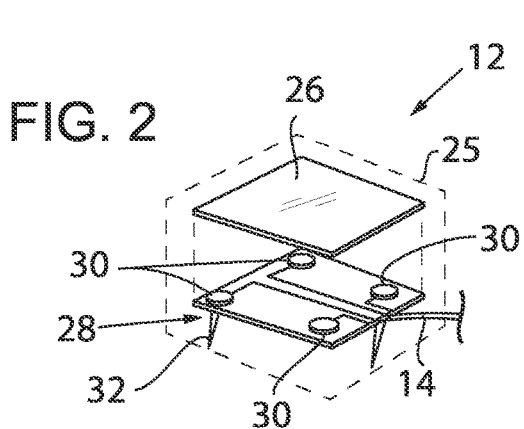
FIG. 2 is an exploded view of one weight plate showing a simple construction supported by load cells.

Referring now to FIG. 2, each weight plate 12 may provide for an upper plate 26, for example, a square, rigid metal plate supported against a rigid base plate 28 of equal size. The upper plate 26 and base plate 28 may be spaced apart using corner-located load cells 30 so that weight on the upper plate 26 may be measured by the load cells 30. The assembly may be placed within a flexible membrane 25 for protection against the elements and held to the ground, for example, by downwardly extending spikes 32 (e.g., lengths of concrete reinforcement bars) or the like.

Figure 3:
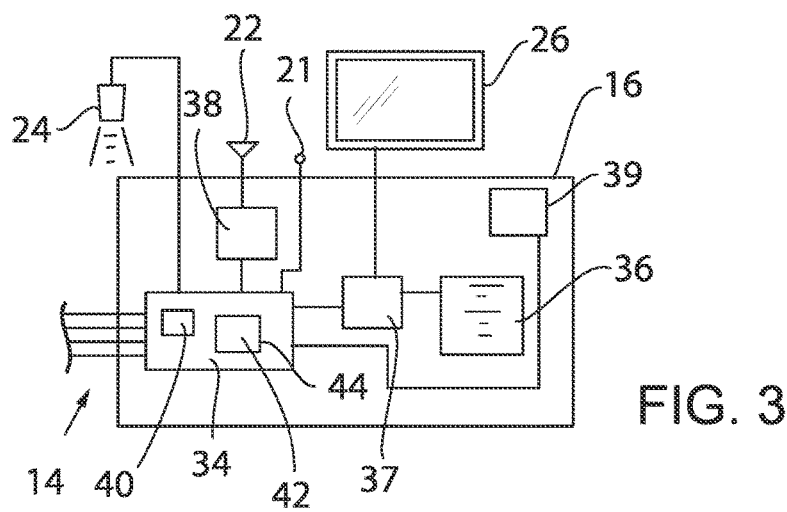
FIG. 3 is a block diagram of circuitry used for processing and transmitting the snowpack measurements.

Referring now to FIG. 3, electrical signals from the four load cells 30 are transmitted over the service cabling 14 to be received by a microcontroller 34 in the control unit 16. The microcontroller 34 may be a general-purpose microcontroller such as an Arduino-compatible micro controller widely commercially available having analog-to-digital converter capabilities for making measurements signals from the load cells 30 of each weight plate 12. The signals can be digitized for further processing as will be discussed below.

The microcontroller 34 may receive power from a battery system 36 (for example, including rechargeable lead acid or lithium ion batteries) via a power management circuit 37 operating to charge and control the discharge of the battery system 36 and employing power from the solar panel 20 for recharge. The microcontroller 34 may also communicate with the temperature sensor 21 and a telemetry device 38 communicating through the antenna 22. The telemetry device 38 may be, for example, a satellite communication system, for example, using Iridium Short-Burst Data Services using an Iridium 9602 Transceiver providing a reliable low-cost data transmission throughout the day. Telemetry devices 38 suitable for this purpose are commercially available under the tradename of "Rock Block" commercially available from Rock Seven of Hampshire, UK. In addition, the microcontroller 34 may control and receive signals from the ultrasound height sensor 24. Optionally a GPS subsystem 39 may be included in the control unit 60 in communication with the microcontroller 34 to assist in locating the snowpack measurement site 10, for example, for service or routine upkeep or if it the control unit 16 becomes dislodged by snow movement or the like. Output from the GPS subsystem 39 may be communicated through the telemetry device 38.

Figure 4:
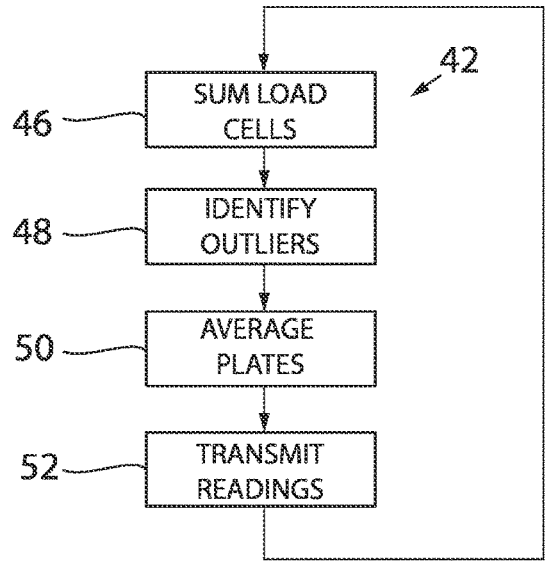
FIG. 4 is a flowchart of a program executed by the circuitry of FIG. 3 in processing the data from the weight plates to provide a robust snowpack measurement.

Referring now to FIGS. 3 and 4, the microcontroller 34 may include a processor 40 executing a program 42 stored in memory 44 for coordinating the operation of the above-described components.

As indicated by process block 46, the microcontroller 34 may first receive the signals from each load cell 30 and combine them, for example, by simple summation to provide a weight reading. This step may include using internal calibration tables for each weight plate 12 to correct for nonlinearities and offsets or the like.

At process block 48 outlier weight measurements from one of the weight plates 12 may be identified, for example, as measurements that deviate by more than a predetermined percentage threshold from an average of the weight measurements of each weight plate 12 which are expected to be similar. Other identification techniques may be used including analyzing time series of weight change on the weight plates 12, such as may reveal the occurrence of a snow bridge formation which will significantly change the history of weight recorded with respect to a bridged weight plate 12 compared to the other weight plates 12. For example, a snow bridge may be indicated on three of the plates indicate a rising weight value while one of the plate ceases to rise in weight value irrespective of the absolute weight on each weight plate. In addition, the individual load cells 30 may be analyzed for off-center loads that may suggest a snow bridge. This off-center weight can be determined when the weight plates have multiple load cells for example in each corner that allow off-center determination of the weight by variations in the readings of the load cells.

Once the outlying measurements have been identified, if any, at process block 50 the readings for the remaining weight plates 12 may be averaged to provide improved representation of the region of the weight plate 12 and this information transmitted as indicated by process block 52 using the telemetry device 38. At the same time, temperature measurements, system status, battery charge, snow height, and the like may also be transmitted.

Generally, the program of process blocks 46-52 may be repeated on a regular basis in between which the system may move to a low power sleep state to conserve battery power.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A snowpack measuring system comprising:
   an array of at least two weight plates positioned in horizontal separation along a plane of ground in an array region, each weight plate including an upper plate for receiving snow thereon and positioned above a base plate and separated from the base plate by at least one load cell providing a weight signal indicating a weight on the upper plate; and
   a processor receiving the weight signal from the load cells of each of the at least two weight plates and executing a program stored in non-transitory memory to combine the weight signals from the at least two weight plates to provide a weight representation of the snowpack in the array region.

2. The system of claim 1 wherein the array region has an area less than 10 meters by 10 meters.

3. The system of claim 1 wherein an area of each of the at least two weight plates is between 1 square foot and 4 square feet.

4. The system of claim 1 wherein the processor executes the program stored in memory to average the weight signals of the at least two weight plates to provide the weight representation.

5. The system of claim 4 wherein the system includes at least three weight plates and the processor executes the program stored in memory to identify an outlier weight signal deviating by more than a predetermined percentage threshold from the weight representation and removing the outlier weight signal from the weight representation.

6. The system of claim 1 wherein the processor executes the program stored in memory to analyze a time series of weight change on the weight plates to reveal an occurrence of a snow bridge formation conducting the weight of the snow away from the weight plates.

7. The system of claim 6 wherein the processor executes the program stored in memory to analyze off-center loads on the weight plates to reveal an occurrence of the snow bridge formation.

8. The system of claim 1 further comprising a control unit communicating with the at least two weight plates and including an antenna configured for over-the-air transmission of data.

9. The system of claim 8 further comprising a solar panel providing power to the control unit.

10. The system of claim 8 further comprising a height sensor measuring a height of the snow above the base plate and configured to communicate the height to the control unit.

11. The system of claim 8 further comprising a GPS system communicating a location signal through the antenna representing a location of the weight plate.

12. The system of claim 8 further comprising a temperature sensor measuring an air temperature and configured to communicate the air temperature to the control unit.

13. The system of claim 1 wherein the load cells are arranged at corners of the weight plate.

14. The system of claim 13 wherein the load cells are covered by a flexible membrane providing protection from environmental elements.

15. The system of claim 14 wherein the weight plates are held to the ground by downwardly extending spikes.

16. A method of measuring an accumulation of snow in a region comprising:

arranging an array of at least two weight plates in horizontal separation along a plane of ground in an array region, each weight plate including an upper plate for receiving snow thereon and positioned above a base plate and separated from the base plate by at least one load cell providing a weight signal indicating a weight on the upper plate;

receiving the weight signal from the load cells of each of the at least two weight plates; and combining the weight signals from the at least two weight plates to provide a weight representation of the snowpack in the array region.

17. The method of claim 16 wherein the combining of the weight signals includes an averaging of the weight signals from the at least two weight plates to provide the weight representation of the accumulation of snow in the region of the array.

18. The method of claim 16 further comprising communicating the weight representation of the accumulation of snow in the region of the array through a telemetry device.

* * * * *